(12) United States Patent
Sato (10) Patent No.: US 9,164,118 B2
(45) Date of Patent: Oct. 20, 2015

(54) SENSOR UNIT AND MOTION ANALYSIS DEVICE

(71) Applicant: Seiko Epson Corporation, Tokyo (JP)

(72) Inventor: Masatoshi Sato, Hashima (JP)

(73) Assignee: Seiko Epson Corporation (JP)

( * ) Notice: Subject to any disclaimer, the term of this patent is extended or adjusted under 35 U.S.C. 154(b) by 224 days.

(21) Appl. No.: 13/886,562

(22) Filed: May 3, 2013

(65) Prior Publication Data

US 2013/0298668 A1 Nov. 14, 2013

(30) Foreign Application Priority Data

May 11, 2012 (JP) ................................ 2012-109189

(51) Int. Cl.
| G01P 1/02 | (2006.01) |
| G01P 13/00 | (2006.01) |
| G01L 5/10 | (2006.01) |
| G01L 1/18 | (2006.01) |
| A61B 5/00 | (2006.01) |
| A61B 5/11 | (2006.01) |

(52) U.S. Cl.
CPC ... *G01P 1/02* (2013.01); *A61B 5/11* (2013.01); *A61B 5/6895* (2013.01); *A61B 5/721* (2013.01); *G01L 1/18* (2013.01); *G01L 5/10* (2013.01); *G01P 13/00* (2013.01)

(58) Field of Classification Search
CPC ....... G01P 1/023; G01P 15/0802; G01P 1/02; G01P 15/18; G01P 3/443; G01P 1/026

USPC .................................................. 73/493, 494
See application file for complete search history.

(56) References Cited

U.S. PATENT DOCUMENTS

| 6,614,108 | B1 * | 9/2003 | Sanftleben et al. ........... 257/710 |
| 8,057,482 | B2 * | 11/2011 | Stone et al. .................... 606/102 |
| 2005/0081628 | A1 * | 4/2005 | Nozoe et al. ..................... 73/494 |
| 2007/0256498 | A1 * | 11/2007 | Yamaji et al. ............... 73/504.16 |
| 2010/0050787 | A1 * | 3/2010 | Abert et al. .............. 73/862.626 |
| 2012/0090409 | A1 * | 4/2012 | Luthje et al. ............. 73/862.627 |
| 2012/0092178 | A1 * | 4/2012 | Callsen et al. ................ 340/669 |
| 2014/0260637 | A1 * | 9/2014 | Molinari ......................... 73/646 |

FOREIGN PATENT DOCUMENTS

| JP | 04141186 | 5/1992 |
| JP | 2008-073210 A | 4/2008 |
| JP | 2009-125499 A | 6/2009 |
| JP | 2009-125507 A | 6/2009 |
| JP | 2009-273551 A | 11/2009 |

* cited by examiner

*Primary Examiner* — Helen Kwok
(74) *Attorney, Agent, or Firm* — Harness, Dickey & Pierce, P.L.C.

(57) ABSTRACT

A sensor unit includes a motion sensor which detects a motion of an object, outputs a detection value, and is mounted on the object through an attachment, a filter which receives the detection value, passes a given frequency band, and is able to change a cutoff frequency of the frequency band, and a control unit which controls the cutoff frequency, wherein the control unit determines the cutoff frequency in accordance with hardness of the attachment.

9 Claims, 9 Drawing Sheets

FIG. 9

SENSOR UNIT AND MOTION ANALYSIS DEVICE

BACKGROUND

1. Technical Field

The present invention relates to a sensor unit, a motion analysis device using the sensor unit, and the like.

2. Related Art

In a motion sensor which detects a motion of an object, the accuracy of a motion to be detected may change depending on a mounting method on the object. JP-A-2009-125507 describes a technique in which an object for motion detection is a person who makes a golf swing, and a motion sensor is put directly on the ear to detect an accurate motion of a head of the person.

However, when an object is a person, the person may be unwilling to bring the motion sensor into direct contact with the skin. When an object is, for example, an expensive item or a precious item, there is a need for avoiding the direct attachment of the motion sensor to the object. Even when an object is an item which is used in an athletic competition, the mounting of the motion sensor during the competition is banned by regulations, and there is a need for facilitating attachment and detachment. In this case, the motion sensor may be mounted on the object through an attachment, and there is a demand for detecting an accurate motion through the attachment.

The attachment is not limited to a hard fixing instrument. For example, when an object is a person, the person puts the gloves to which the motion sensor is attached, and the motion of the person is detected. At this time, the attachment is the soft gloves. The material for the attachment may change depending on the object for motion detection, or may be selected from a plurality of materials.

Noise which occurs due to the movement of the object is transferred to the motion sensor through the attachment. For example, a motion sensor is mounted on a skate blade through an attachment to detect a motion of an athlete. At this time, high-frequency noise which occurs due to minute unevenness of an ice surface is transferred to the motion sensor.

However, noise may be most absorbed or may not be absorbed by the attachment depending on hardness of the attachment. Accordingly, even when a sensor unit which includes a motion sensor and a filter passing a prescribed frequency band is used, if the type of the attachment changes, it is difficult to detect an accurate motion of an object to be measured.

SUMMARY

An advantage of some aspects of the invention is that it provides a sensor unit capable of detecting an accurate motion of an object to be measured without depending on the type of an attachment, and a motion analysis device using the sensor unit.

(1) An aspect of the invention is directed to a sensor unit including a motion sensor which is mounted on an object through an attachment, a filter which receives a detection value from the motion sensor, passes a given frequency band, and is able to change a cutoff frequency of the frequency band, and a control unit which controls the cutoff frequency, wherein the control unit determines the cutoff frequency in accordance with hardness of the attachment.

(2) The sensor unit may further include a storage unit which stores table information, in which the cutoff frequency is determined in accordance with hardness of the attachment, wherein the control unit may control the cutoff frequency using the table information.

The sensor unit includes the motion sensor, the filter which receives the detection value from the motion sensor, and passes the given frequency band, and the control unit which controls the cutoff frequency. The motion sensor is, for example, an acceleration sensor, an angular rate sensor, or the like, and detects an acceleration, an angular rate, or the like by a motion of an object to be measured and outputs the detection value. The motion of the object is, for example, movement in a direction along the axis of the motion sensor, or rotation around the axis. The motion sensor may include a plurality of types of sensors.

The filter is, for example, a band-pass filter, receives the detection value from the motion sensor, and passes only a specific frequency band. The filter may be a high-pass filter or a low-pass filter. At this time, the cutoff frequency of the filter is variable. The cutoff frequency can be adjusted in accordance with the type of the attachment which attaches the motion sensor to the object.

With the adjustment of the cutoff frequency, it is possible to appropriately remove noise which differs depending on the type of the attachment and is transferred to the motion sensor. Therefore, with the sensor unit according to the aspect of the invention, it is possible to realize the sensor unit capable of detecting an accurate motion of an object to be measured without depending on the type of the attachment.

The sensor unit includes the motion sensor and the filter. For this reason, in the sensor unit in which the motion sensor and the filter are packaged, the attachment which attaches the motion sensor to the object means the attachment of the sensor unit. However, the sensor unit may have a configuration in which only the motion sensor is attached independently to the object.

The sensor unit includes the control unit which generates a control signal for changing the cutoff frequency. The control unit receives a hardness signal representing hardness of the attachment. The control signal may be generated using a table in which the cutoff frequency according to hardness of the attachment is determined.

The sensor unit includes the control unit, whereby an appropriate cutoff frequency is selected in accordance with the hardness signal after the sensor unit is attached to the object. The control unit may be an arithmetic processing unit, such as a CPU.

The hardness signal may be generated inside the sensor unit or may be given from the outside of the sensor unit. The control unit may use the table information in which the cutoff frequency is determined in accordance with hardness of the attachment. The table information may be stored in a storage unit inside the control unit or may be stored in a storage unit outside the control unit. The storage unit may include a RAM or a ROM, and the type is not limited to a specific thing. When a ROM is included, the table information may be written at the time of manufacturing of the sensor unit, and when a RAM is included, the table information may be written from the outside of the sensor unit at the time of the activation of the sensor unit.

(3) The sensor unit may further include a pressure sensor, wherein the pressure sensor may measure a pressure value when the sensor unit is attached to the attachment and may output the pressure value to the control unit.

(4) In the sensor unit, the pressure sensor may be a piezoresistive pressure sensor.

With these configurations, the hardness signal which is received such that the control unit generates the control signal is a pressure value from the pressure sensor. The pressure sensor measures the pressure of the attachment. For this reason, even when the sensor unit is mounted on the object through any attachment, the control unit can generate an appropriate control signal on the basis of the measured pressure of the attachment.

At this time, the pressure sensor may be a piezoresistive pressure sensor. The piezoresistive pressure sensor can be manufactured using semiconductor manufacturing technology, is compact, and performs accurate detection.

The pressure sensor may be a pressure sensor of a type other than a piezoresistive pressure sensor. For example, the pressure sensor may be a spring pressure sensor which uses the elastic force of a spring or may be a liquid crystal pressure sensor which uses change in the electric constant of liquid crystal or the like.

(5) The sensor unit may further include an operating unit which receives information regarding hardness of the attachment from the outside of the sensor unit and outputs the information regarding hardness to the control unit.

With this configuration, the sensor unit includes the operating unit which receives information from the outside of the sensor unit and outputs an instruction signal. For this reason, it becomes possible to designate the cutoff frequency according to hardness of the attachment from the outside of the sensor unit. For example, when the type of the attachment is determined in advance, the pressure sensor may not be included in the sensor unit, thereby suppressing manufacturing costs of the sensor unit. For example, the information to be received may be the information regarding hardness of the attachment or may be indirect information, such as a setting instruction from a user.

(6) In the sensor unit, when it is determined that the attachment is harder than predetermined hardness, the control unit may generate the control signal such that the cutoff frequency of the high-frequency band is lowered.

(7) In the sensor unit, when it is determined that the attachment is softer than predetermined hardness, the control unit may generate the control signal such that the cutoff frequency of the low-frequency band is lowered.

With this configuration, when it is determined that the attachment is harder than the predetermined hardness, the control unit generates the control signal such that the cutoff frequency of the high-frequency band is lowered. When the attachment is hard, high-frequency noise is likely to be transferred to the motion sensor. At this time, the cutoff frequency of the high-frequency band is lowered to reduce the influence of noise, whereby an accurate motion of an object to be measured can be detected.

When it is determined that the attachment is softer than predetermined hardness, the control unit may generate the control signal such that the cutoff frequency of the low-frequency band is lowered. When the attachment is soft, an accurate motion of an object to be measured including a motion of a low frequency to be transferred to the motion sensor can be detected.

The predetermined hardness may be determined by a preliminary experiment or may be obtained by calculating using hardness. A plurality of hardness serving as a threshold value may be determined, and the cutoff frequency may be adjusted in a multilevel manner.

(8) Another aspect of the invention is directed to a motion analysis device including the above-described sensor unit.

With this configuration, it is possible to realize a motion analysis device which is capable of detecting an accurate motion of an object to be measured without depending on the type of the attachment of the sensor unit. The motion analysis device is, for example, a device which analyzes swing of golf or tennis, batting of baseball, sliding of figure skating, running of running exercise, or the like and uses the analysis to improve athletic skills. For example, when the sensor unit of the motion analysis device according to the aspect of the invention is attached to figure skates, it is possible to realize a motion analysis device in which high-frequency noise which occurs due to minute unevenness of the surface is cut, thereby analyzing an accurate motion of an athlete.

BRIEF DESCRIPTION OF THE DRAWINGS

The invention will be described with reference to the accompanying drawings, wherein like numbers reference like elements.

DESCRIPTION OF EXEMPLARY EMBODIMENTS

A preferred embodiment of the invention will be described in detail with reference to the drawings. The following embodiment is not intended to unduly limit the content of the invention described in the appended claims. It is not always true that all elements described below are essential constituent elements of the invention.

1. CONFIGURATION OF SENSOR UNIT

Figure 1:
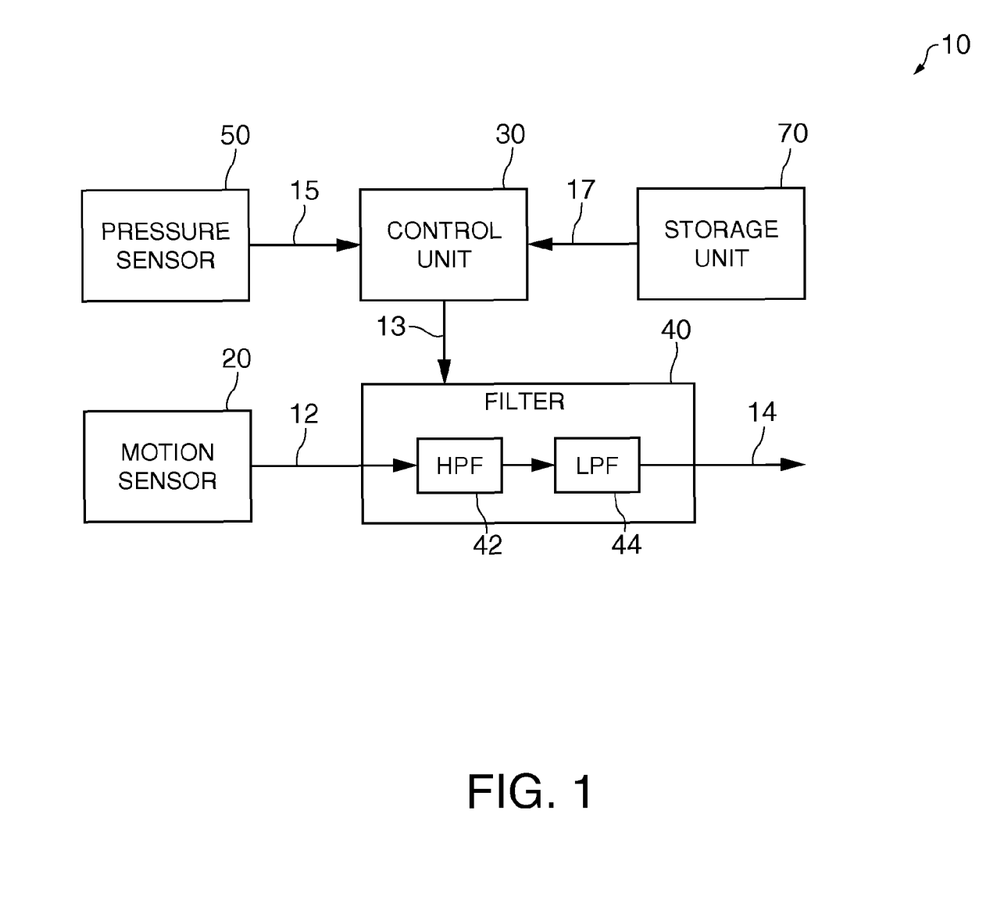
FIG. 1 is a block diagram of a sensor unit of this embodiment.

FIG. 1 is a block diagram of a sensor unit 10 of one preferred embodiment. As shown in FIG. 1, the sensor unit 10 of this embodiment has a motion sensor 20, a control unit 30, a filter 40, a pressure sensor 50, and a storage unit 70. The sensor unit 10 is mounted on an object to be measured of the motion sensor 20 through an attachment.

The filter 40 includes an HPF 42 (high-pass filter) and an LPF 44 (low-pass filter), and realizes a band-pass filter.

The motion sensor 20 is, for example, an acceleration sensor, an angular rate sensor, or the like, detects an acceleration, an angular rate, or the like by a motion of a person or a thing as an object to be measured (hereinafter, referred to as an object), and outputs a detection value 12. A predetermined motion is, for example, movement in a direction along the axis of the motion sensor 20 or rotation around the axis.

The motion sensor 20 may include a plurality of types of sensors. In this embodiment, it is assumed that a triaxial acceleration sensor and a triaxial angular rate sensor are included, and various motions of the object are detected. The detection value 12 may express the detected motion by, for example, change in the voltage value.

The filter 40 is a band-pass filter, receives the detection value 12 from the motion sensor 20, passes only a specific frequency band, and outputs the frequency band as an output signal 14. The filter 40 has the high-pass filter (HPF 42) and the low-pass filter (LPF 44) in combination to constitute a band-pass filter. At this time, both the cutoff frequency (corresponding to the cutoff frequency of the low-frequency band) of the HPF 42 and the cutoff frequency (corresponding to the cutoff frequency of the high-frequency band) of the LPF 44 change independently in response to a control signal 13 from the control unit 30. The control signal 13 changes depending on the type of an attachment (that is, an attachment of the sensor unit 10) which is used to attach the motion sensor 20 to the object, whereby the cutoff frequencies of the HPF 42 and the LPF 44 are adjusted.

These cutoff frequencies are adjusted, whereby it is possible to appropriately remove noise which differs depending on the type of the attachment and is transferred to the motion sensor 20. Accordingly, the sensor unit 10 can detect an accurate motion of the object without depending on the type of the attachment.

The control unit 30 receives a hardness signal 15 which represents hardness of the attachment. The control unit 30 receives table information 17 from the storage unit 70 and generates the control signal 13. In the table information 17, the cutoff frequency according to hardness of the attachment is determined. It is assumed that the control unit 30 of this embodiment is a CPU.

The pressure sensor 50 measures the pressure of the attachment and outputs a pressure value. Since the pressure value changes depending on hardness of the attachment, the pressure value from the pressure sensor 50 becomes the hardness signal 15. The pressure sensor 50 is included, whereby the pressure of the attachment can be measured. For this reason, even if the sensor unit 10 is mounted on the object through any attachment, the control unit 30 can generate the appropriate control signal 13 on the basis of the hardness signal 15 obtained by measurement.

The pressure sensor 50 is a piezoresistive pressure sensor. The piezoresistive pressure sensor can be manufactured using semiconductor manufacturing technology, is compact, and can perform accurate detection.

The storage unit 70 stores a table which is used when the control unit 30 generates the control signal 13. The storage unit 70 may store a program which executes arithmetic processing when the control unit 30 serving as a CPU generates the control signal 13. The storage unit 70 includes a RAM or a ROM which stores data or the program.

2. DETAILS OF FILTER

Figure 2:
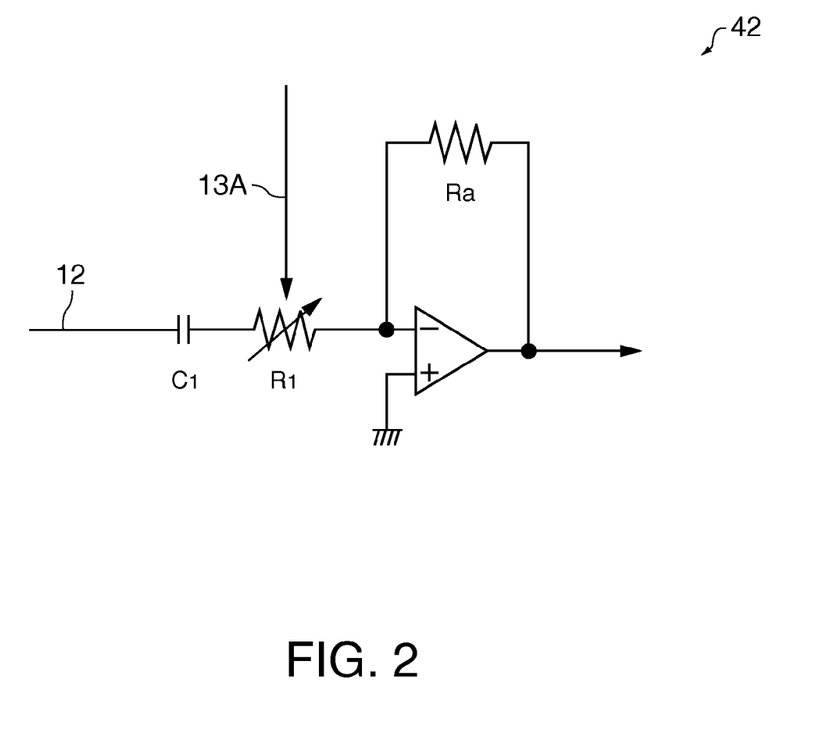
FIG. 2 is a diagram showing a configuration example of a high-pass filter.

FIG. 2 is a diagram showing a configuration example of the high-pass filter (HPF 42). In the detection value 12 from the motion sensor 20, a frequency component higher than the cutoff frequency of the low-frequency band passes through the HPF 42. The cutoff frequency $f_{cl}$ of the low-frequency band is expressed by Expression (1).

$$f_{cl} = \frac{1}{2\pi R_1 C_1} \quad (1)$$

Here, $R_1$ is the resistance value of a variable resistor which changes with a control signal 13A (a signal of part of the control signal 13 of FIG. 1). Accordingly, the control unit 30 can adjust the cutoff frequency $f_{cl}$ of the low-frequency band with the control signal 13A.

The variable resistor may be constituted by, for example, integrating the control signal 13A, which is a PWM signal generated on the basis of the hardness signal 15, by an integration circuit and inputting the resultant signal to the gate of a transistor, or may be constituted by other circuits.

For example, when it is determined that hardness of the attachment is softer than predetermined hardness, the control unit 30 may generate the control signal 13A such that the cutoff frequency $f_{cl}$ of the low-frequency band is lowered. At this time, a motion of a low frequency to be transferred to the motion sensor 20 when a soft attachment (for example, sponge or rug) is used is also included in the output signal 14, whereby an accurate motion of the object can be detected.

In contrast, when it is determined that hardness of the attachment is harder than the predetermined hardness, the control unit 30 may generate the control signal 13A such that the cutoff frequency $f_{cl}$ of the low-frequency band increases. At this time, the influence of noise of a low frequency to be transferred to the motion sensor 20 through the hard attachment (for example, metal plate or wooden board) can be reduced.

The control unit 30 may adjust the cutoff frequency $f_{cl}$ of the low-frequency band by changing $C_1$ with the control signal 13A. The predetermined hardness may be measured using a material which can be used as the attachment, and may be determined by how much noise is transferred to the motion sensor 20. For example, the predetermined hardness may be determined to hardness of skin or felt, and different control signals 13A may be generated in accordance with hardness is softer or harder than the predetermined hardness.

Figure 3:
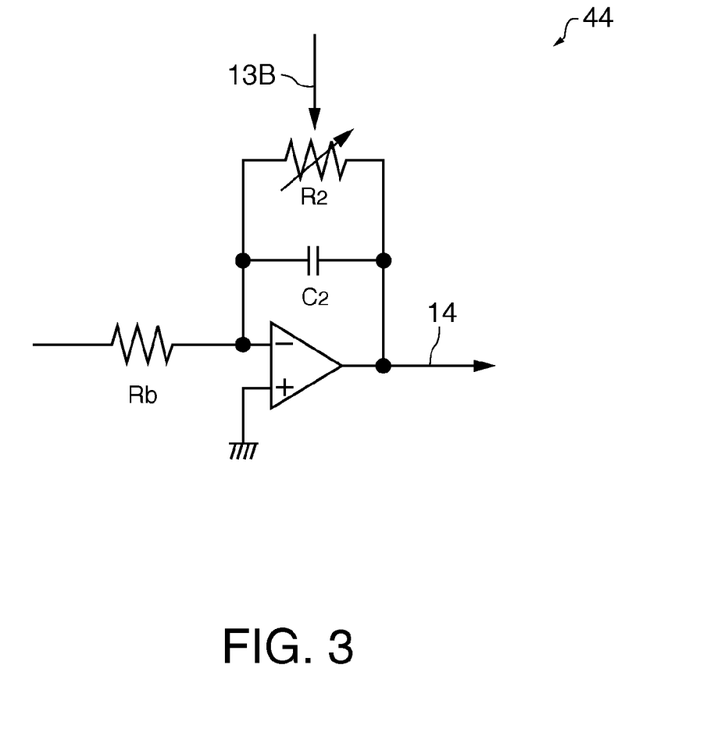
FIG. 3 is a diagram showing a configuration example of a low-pass filter.

FIG. 3 is a diagram showing a configuration example of the low-pass filter (LPF 44). At this time, in a signal which passes through the HPF 42, a frequency component lower than the cutoff frequency of the high-frequency band passes through the LPF 44. The cutoff frequency $f_{ch}$ of the high-frequency band is expressed by Expression (2).

$$f_{ch} = \frac{1}{2\pi R_2 C_2} \quad (2)$$

Here, $R_2$ is the resistance value of a variable resistor which changes with a control signal 13B (a signal of part of the control signal 13 of FIG. 1). Accordingly, the control unit 30 can adjust the cutoff frequency $f_{ch}$ of the high-frequency band with the control signal 13B. The configuration of the variable resistor may be the same as or different from the HPF 42. The control unit 30 may adjust the cutoff frequency $f_{ch}$ of the high-frequency band by changing $C_2$ with the control signal 13B.

For example, when it is determined that hardness of the attachment is harder than predetermined hardness, the control unit 30 may generate the control signal 13B such that the cutoff frequency $f_{ch}$ of the high-frequency band is lowered. At this time, the influence of noise of a high frequency to be transferred to the motion sensor 20 through the hard attachment is reduced, whereby an accurate motion of the object can be detected. The predetermined hardness may be determined to be the same as in the HPF 42.

In contrast, when it is determined that hardness of the attachment is softer than the predetermined hardness, the control unit 30 may generate the control signal 13B such that the cutoff frequency $f_{ch}$ of the high-frequency band increases.

At this time, since high-frequency noise is difficult to be transferred to the motion sensor 20 by the soft attachment, many high-frequency components are included in the output signal 14, and the detected motion of the object can be ensured more accurately.

Figure 8:
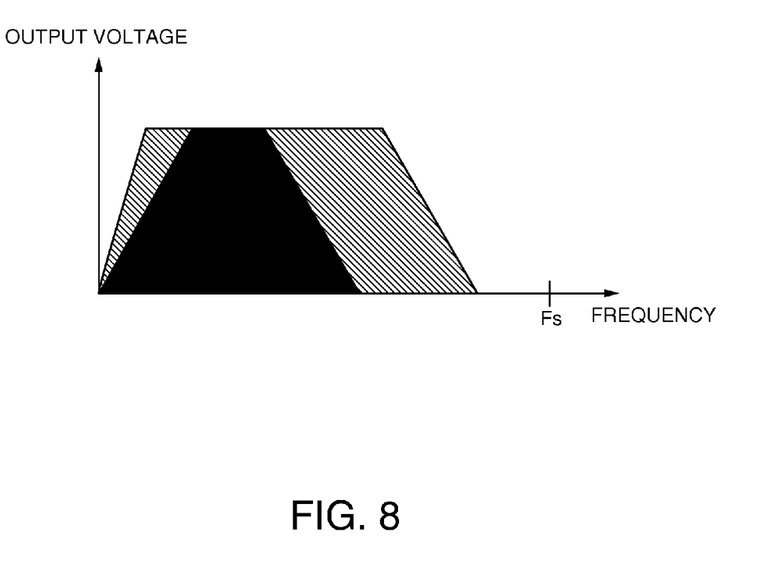
FIG. 8 is a diagram showing the relationship between hardness of an attachment and characteristics of a filter.

The characteristics of the filter 40 having the HPF 42 and the LPF 44 are as shown in FIG. 8. The relationship between the voltage (output voltage) and the frequency of the output signal 14 from the filter 40 is as indicated by a black portion of FIG. 8 when hardness of the attachment is harder than the predetermined hardness. That is, the cutoff frequency $f_{ch}$ of the high-frequency band is set to be significantly lower than a sampling frequency Fs. The cutoff frequency $f_{cl}$ of the low-frequency band is set to be higher.

When hardness of the attachment is softer than the predetermined hardness, the relationship is as indicated by a hatched portion of FIG. 8. In both the high-frequency band and the low-frequency band, a passable band is widened. That is, when a soft attachment which is difficult to transfer noise is used, the passable band is widened, whereby a more accurate motion of the object can be detected.

3. DETAILS OF PRESSURE SENSOR

In order to select an appropriate cutoff frequency in accordance with the attachment, the hardness signal 15 should be accurate. In the sensor unit 10 of this embodiment, the pressure value from the pressure sensor 50 becomes the hardness signal 15. Accordingly, the pressure sensor 50 should accurately output hardness of the attachment as the pressure value.

In the sensor unit 10 of this embodiment, the pressure sensor 50 is a piezoresistive pressure sensor, is compact, and can perform accurate detection.

Figure 4:
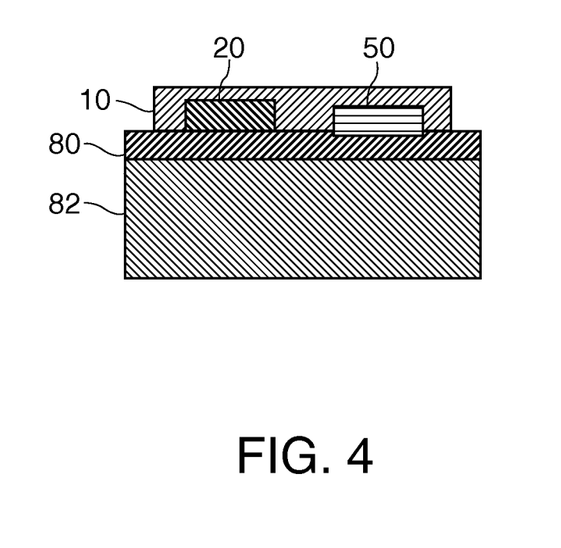
FIG. 4 is a contact sectional view of the sensor unit of this embodiment.

FIG. 4 is a sectional view showing a state where the sensor unit 10 of this embodiment is in contact with an object 82 (an object to be measured; for example, the object may be a person, and in this embodiment, it is assumed that the object is a thing) through an attachment 80. The motion sensor 20 in the sensor unit 10 is in contact with the attachment 80 so as to accurately detect the motion of the object 82. The pressure sensor 50 in the sensor unit 10 is in contact with the attachment 80 such that a diaphragm 52 (see FIG. 5) is pushed into the attachment 80.

Figure 5:
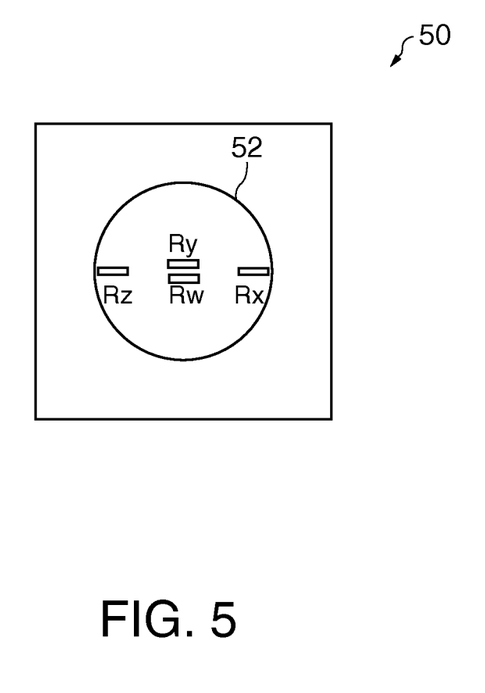
FIG. 5 is a diagram showing a configuration example of a pressure sensor.

FIG. 5 is a plan view of the pressure sensor 50 which is a piezoresistive pressure sensor. The pressure sensor 50 includes a pressure receiver (diaphragm 52), and piezoresistance is formed on the diaphragm 52. If a pressure is applied to the diaphragm 52, resistivity changes with stress applied to the piezoresistance. With this, the pressure is detected.

Figure 6:
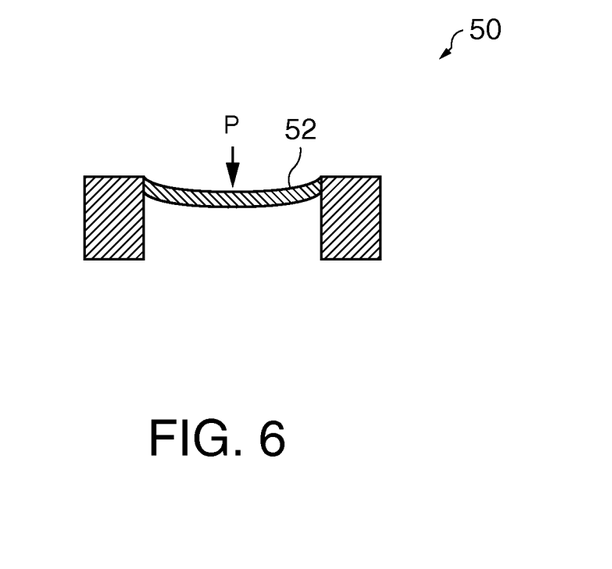
FIG. 6 is a sectional view illustrating a diaphragm of a pressure sensor.

FIG. 6 is a sectional view showing a state where a pressure P is applied to the pressure sensor 50. At this time, the pressure P is the force which is generated when the attachment 80 pushes back the pressure sensor 50. When the attachment 80 is soft, the attachment 80 behaves as a cushion material, the pressure P decreases. That is, the pressure P is measured, whereby hardness of the attachment 80 can be detected.

Returning to FIG. 5, rectangles shown in FIG. 5 denote piezoresistance, and the resistance values thereof are Rx, Ry, Rz, and Rw. A Wheatstone bridge is constituted by the piezoresistance, and for example, if a constant current flows, an output potential difference proportional to a pressure is obtained.

Figure 7:
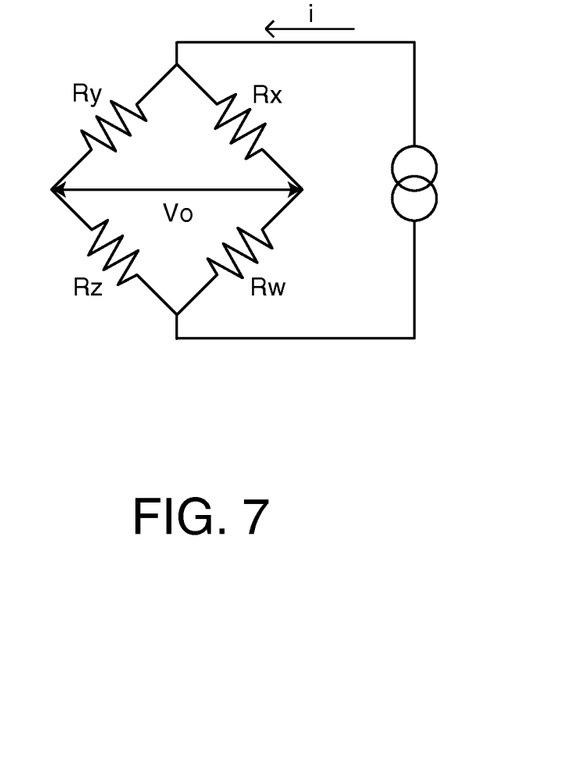
FIG. 7 is a diagram illustrating a circuit which detects a pressure of a pressure sensor.

FIG. 7 is a diagram showing a Wheatstone bridge which is constituted by the piezoresistance formed on the diaphragm 52 of the pressure sensor 50. A current i flows from a constant current source into the Wheatstone bridge. At this time, an output potential difference Vo is measured, whereby the pressure from the attachment 80 can be known. That is, hardness of the attachment 80 can be known. The output potential difference Vo is expressed by Expression (3).

$$V_O = \frac{RxRz - RyRw}{Rx + Ry + Rz + Rw} \quad (3)$$

In this way, in the sensor unit 10 of this embodiment, hardness of the attachment 80 can be detected by the pressure sensor 50. At this time, the control unit 30 receives the output potential difference Vo (pressure value) as the hardness signal 15. The storage unit 70 stores a table in which the cutoff frequency according to the pressure value is determined. The control unit 30 can efficiently generate the control signal 13 using the table. The table which is stored in the storage unit 70 may be a table in which the control signal 13 according to the pressure value is determined. At this time, the control unit 30 can generate the control signal 13 more efficiently.

As described above, the sensor unit 10 of the embodiment can change the filter characteristics in conformity with the detected hardness of the attachment 80. That is, it is possible to realize a sensor unit capable of detecting an accurate motion of an object to be measured without depending on the type of the attachment 80.

4. MODIFICATION EXAMPLE

In the foregoing embodiment, the pressure sensor 50 measures hardness of the attachment 80. However, for example, when the type of the attachment 80 is determined in advance, it is efficient to designate the type of the attachment 80 from the outside of the sensor unit 10. At this time, the pressure sensor 50 may not be included in the sensor unit 10, whereby manufacturing costs of the sensor unit 10 can be suppressed.

Figure 9:
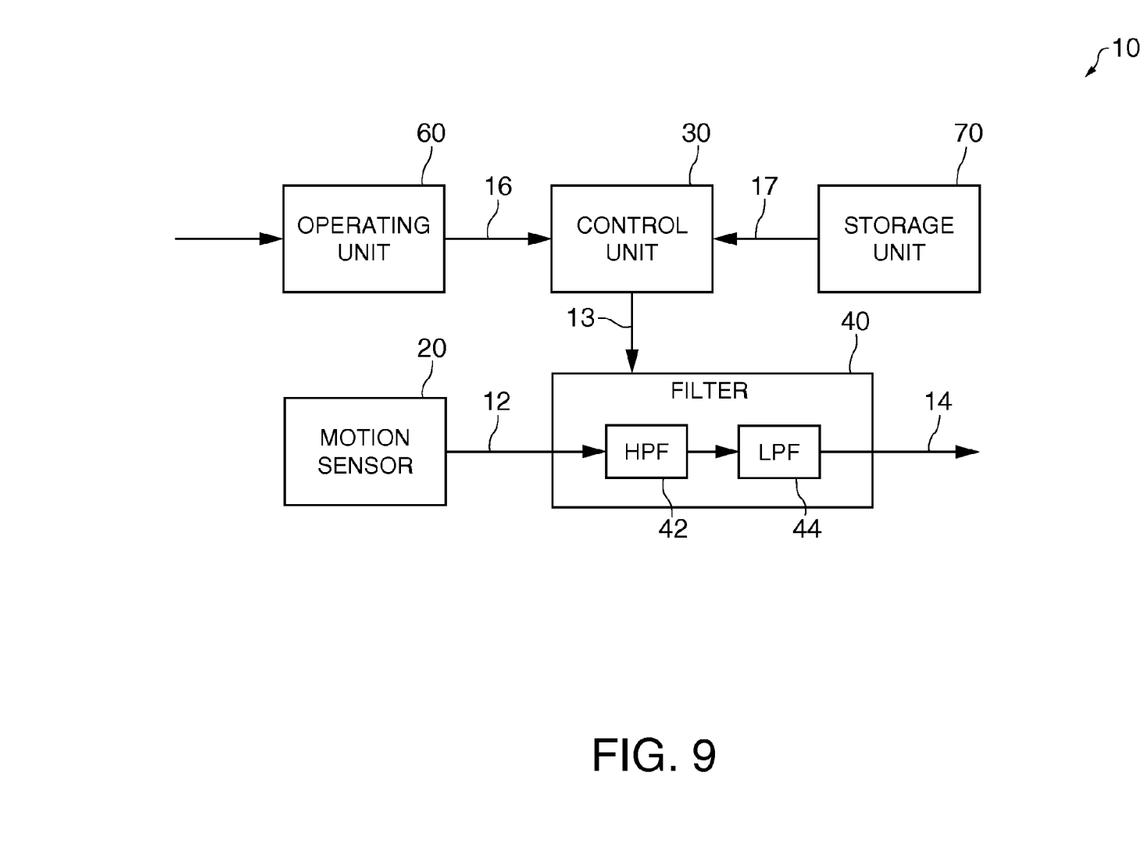
FIG. 9 is a block diagram of a sensor unit of a modification example.

As shown in FIG. 9, a sensor unit 10 of this modification example includes an operating unit 60 which receives an instruction from the outside of the sensor unit 10 and generates an instruction signal, instead of the pressure sensor 50. The operating unit 60 outputs the instruction signal as a hardness signal 16. For example, it is assumed that the type of the attachment 80 is determined in advance into three types of (A) plate, (B) skin or felt, and (C) rug. A user who mounts the sensor unit 10 of this modification example on the object 82 through the attachment 80 of skin designates (B) skin or felt as an instruction to the sensor unit 10 using the operating unit 60. When this happens, the control unit 30 receives the content (that is, the attachment 80 is skin or felt) designated by the user as the hardness signal 16. The control unit 30 can generate the appropriate control signal 13.

The operating unit 60 may be a button, a slide switch, or the like, or may be a touch panel. Except that the operating unit 60 is included, the sensor unit 10 of this modification example is the same as in the foregoing embodiment, and description thereof will not be repeated.

5. APPLICATION EXAMPLE

The sensor unit 10 of this embodiment can be suitably used in, for example, a motion analysis device. The motion analysis device is, for example, a device which analyzes swing of golf or tennis, batting of baseball, sliding of figure skating, running of running exercise, or the like, and uses the analysis to improve athletic skills.

For example, even when the sensor unit 10 which is part of the motion analysis device is attached to a figure skates through the hard attachment 80, the motion analysis device of this application example cuts high-frequency noise which occurs due to minute unevenness of the surface, thereby analyzing an accurate motion of an athlete.

For example, when the sensor unit 10 which is part of the motion analysis device is attached to a golf club or a tennis racket through the attachment 80 of sponge or the like, the motion analysis device of this application example also includes a motion of a low frequency to be transferred to the motion sensor 20 in the output signal 14, thereby capturing an accurate trajectory of the gold club or the tennis racket.

An advice (for example, "since there is variation in the outward direction at the time of downward swing of the tennis racket, make a swing while keeping the lower arm tucked in" or the like) necessary for improving athletic skills of an athlete can be showed to the athlete on the basis of the obtained accurate motion of the object to be measured.

6. OTHERS

The invention includes the substantially same configuration (for example, configuration with the same functions, methods, and results or configuration with the same objects and effects) as the configuration described in the embodiment. The invention also includes a configuration in which non-essential portions of the configuration described in the embodiments are replaced. The invention also includes a configuration which can obtain the same functional effects or can attain the same objects as the configuration described in the embodiment. The invention also includes a configuration in which known techniques are added to the configuration described in the embodiment.

The entire disclosure of Japanese Patent Application No. 2012-109189, filed May 11, 2012 is expressly incorporated by reference herein.

What is claimed is:

1. A sensor unit comprising:
   a motion sensor which is mounted on an object through an attachment;
   a filter which receives a detection value from the motion sensor, passes a given frequency band, and is able to change a cutoff frequency of the frequency band; and
   a control unit which controls the cutoff frequency,
   wherein the control unit determines the cutoff frequency in accordance with hardness of the attachment.

2. The sensor unit according to claim 1, further comprising:
   a storage unit which stores table information, in which the cutoff frequency is determined in accordance with hardness of the attachment,
   wherein the control unit controls the cutoff frequency using the table information.

3. The sensor unit according to claim 1, further comprising:
   a pressure sensor,
   wherein the pressure sensor measures a pressure value when the sensor unit is attached to the attachment, and outputs the pressure value to the control unit.

4. The sensor unit according to claim 3,
   wherein the pressure sensor is a piezoresistive pressure sensor.

5. The sensor unit according to claim 1, further comprising:
   an operating unit which receives information regarding hardness of the attachment from the outside of the sensor unit and outputs the information regarding hardness to the control unit.

6. The sensor unit according to claim 1,
   wherein, when the attachment is harder than a predetermined hardness, the control unit generates a control signal such that the cutoff frequency of a high-frequency band is lowered.

7. The sensor unit according to claim 1,
   wherein, when the attachment is softer than a predetermined hardness, the control unit generates a control signal such that the cutoff frequency of a low-frequency band is lowered.

8. A motion analysis device comprising:
   the sensor unit according to claim 1.

9. The sensor unit according to claim 1 wherein the frequency band is defined between a high-cutoff frequency band and a low-cutoff frequency band, and the control unit adjusts at least one of the high-cutoff frequency band or the low-cutoff frequency band to change the cutoff frequency.

* * * * *